United States Patent [19]
Brandt et al.

[11] Patent Number: 5,310,557
[45] Date of Patent: May 10, 1994

[54] SHAPED ARTICLES BASED ON POLYETHER BLOCK AMIDE ELASTOMERS

[75] Inventors: Heinz-Dieter Brandt; Rolf Dhein, both of Krefeld; Herbert Hugl, Bergisch Gladbach; Doris Hackemüller, Düsseldorf; Wilhelm Stendel, Wupperal, all of Fed. Rep. of Germany

[73] Assignee: Bayer Aktiengesellschaft, Leverkusen, Fed. Rep. of Germany

[21] Appl. No.: 971,163

[22] Filed: Nov. 3, 1992

[30] Foreign Application Priority Data

Nov. 13, 1991 [DE] Fed. Rep. of Germany ....... 4137273

[51] Int. Cl.$^5$ ............................................. A01N 25/34
[52] U.S. Cl. ..................................... 424/411; 424/409
[58] Field of Search ......................... 424/486, 407, 411

[56] References Cited

U.S. PATENT DOCUMENTS

| | | | |
|---|---|---|---|
| 3,485,787 | 12/1969 | Haefele et al. | 260/33.6 |
| 3,814,061 | 6/1974 | Aries | 424/28 |
| 3,852,416 | 12/1974 | Grubb et al. | 424/14 |
| 3,918,407 | 11/1975 | Greenberg | 119/156 |
| 3,944,662 | 3/1976 | Miller, Jr. et al. | 424/78 |
| 4,006,116 | 2/1977 | Dominguez | 260/33.6 AQ |
| 4,039,629 | 8/1977 | Himes et al. | 260/876 B |
| 4,041,151 | 8/1977 | Milionis et al. | 424/78 |
| 4,145,409 | 3/1979 | Pasarela | 424/16 |
| 4,158,051 | 6/1979 | Greenberg et al. | 119/106 |
| 4,195,075 | 3/1980 | Miller | 424/14 |
| 4,225,578 | 9/1980 | von Bittera et al. | 424/14 |
| 4,536,388 | 8/1985 | Pearce, III | 424/28 |

FOREIGN PATENT DOCUMENTS 0338821 10/1989 European Pat. Off. .
3611137 10/1986 Fed. Rep. of Germany .

OTHER PUBLICATIONS

Chemical Abstracts, vol. 84, 136532, 1976, p. 37.
Chemical Abstracts, vol. 89, 130402, 1978, p. 35.
Chemical Abstracts, vol. 90, 39419, 1979, p. 10.
Chemical Abstracts, vol. 90, 39666, 1979, p. 29.
Chemical Abstracts, vol. 90, 205147, 1979, p. 46.
Chemical Abstracts, vol. 97, 67843, 1982, p. 214.
Chemical Abstracts, vol. 100, 87033, 1984, p. 63.
Chemical Abstracts, vol. 112, 212524, 1990, p. 222.
Chemical Abstracts, vol. 106, 51349, 1987, p. 49.

*Primary Examiner*—Thurman K. Page
*Assistant Examiner*—Peter F. Kulkosky
*Attorney, Agent, or Firm*—Sprung Horn Kramer & Woods

[57] ABSTRACT

The present invention relates to shaped articles which contain active compounds and are characterized in that they comprise, as carriers, thermoplastic elastomers based on polyether block amides, as well as customary additives if appropriate, and to processes for their production and to their use for control of pests in animals.

13 Claims, No Drawings

SHAPED ARTICLES BASED ON POLYETHER BLOCK AMIDE ELASTOMERS

The present invention relates to new shaped articles which contain active compounds and are based on elastomeric polyether block amides which can be processed as thermoplastics, their production and their use for control of pests, in particular in stock and domestic animals.

Shaped articles which comprise active compounds for controlling pests are known. They are based on the slow release of active compounds from a carrier matrix of plastics which contains active compounds (compare, for example, Aries et al U.S. Pat. No. 3 814 061, Greenberg U.S. Pat. No. 3 918 407, Miller and Morales U.S. Pat. NO. 3 944 662, Millionis and Spicer U.S. Pat. No. 4 041 151, Pasarela U.S. Pat. No. 4 145 409, Greenberg and Cloud U.S. Pat. No. 4 158 051, v. Bittera et al U.S. Pat. No. 4 225 578. McDaniel and Pruitt EP-OS 0 052 411 B1, Grubb et al U.S. Pat. No. 3 852 416 and Pearce U.S. Pat. No. 4 536 388.

The carrier employed practically almost exclusively for known shaped articles is PVC. Although other carriers are mentioned in the literature, as yet they have not found acceptance in practice. Thus, U.S. Pat. No. 4 195 075 mentions, inter alia, that thermoplastic elastomers are also possible as carrier polymers for ear marks. However, this citation also describes exclusively examples using plasticizer-containing PVC as the carrier polymer.

This is also not surprising. PVC is inexpensive and readily accessible. It is also miscible with other substances, in particular plasticizers, within wide limits. These plasticisers in PVC bodies containing active compounds have the function of keeping the active compound dissolved in the carrier and of transporting it slowly to the surface of the body. At the surface, the active compound evaporates or is rubbed off from the surface, together with the plasticiser. The interaction of the three components PVC carrier, plasticiser and active compound determines whether and to what extent the shaped article can be employed in practice.

If one component of the overall system is changed, it can no longer be predicted whether the system still acts in practice. This applies in particular if the plasticiser, which indeed has a key function in transportation of the active compound, is changed or omitted.

For various reasons, it is desirable to replace PVC as the carrier material. It is also advantageous to dispense partly or completely with the use of plasticisers. It was therefore a matter of discovering an active compound/shaped article system in which PVC, as the carrier material, and plasticiser can be dispensed with and which nevertheless has a good action in practice.

Thermoplastic elastomers are materials which comprise elastomeric phases either mixed physically or bonded chemically in polymers which can be processed as thermoplastics. A distinction is made between polyblends, in which the elastomeric phases are present in physically mixed-in form, and block polymers, in which the elastomeric phases are a constituent of the polymeric matrix Hard and soft regions are present side by side as a result of the build-up of the thermoplastic elastomers. The hard regions form a crystalline network structure or a continuous phase, the intestices of which are filled by elastomeric segments. On the basis of this build-up, these materials have rubber-like properties.

A distinction may be made between 5 main groups of thermoplastic elastomers:
1. Copolyesters
2. Polyether block amides (PEBA)
3 Thermoplastic polyurethanes (TPU)
4. Thermoplastic polyolefins (TPO)
5. Styrene block copolymers These 5 main groups show similar macroscopic physical properties, coupled with a completely different chemical build-up. In spite of these macroscopically similar properties, these main groups behave completely differently in respect of mixing in and release of active compounds.

The use of certain thermoplastic elastomers as carriers for active compounds is known, for example, from EP-OS 338 821 and DE-OS (German Published Specification) 3 611 137.

The present invention relates to
1 Shaped articles which contain active compounds and are based on thermoplastic elastomers of the polyether block amide type and which comprise, as the active compounds, insecticidal or acaricidal active compounds having a low vapor pressure, as well as customary additives.
2. Processes for the production of shaped articles containing active compounds, characterized in that thermoplastic elastomers of the polyether block amide type are mixed with insecticidal or acaricidal active compounds having a low vapor pressure and if appropriate customary additives and the mixture is processed in the customary manner.

Shaped articles which contain active compounds and are based on thermoplastic elastomers of the polyether block amide type are known from DE-OS (German Published Specification) 3 611 137. Active compounds having a high vapor pressure, such as, for example, DDVP, were employed in these shaped articles. It was not to be expected that active compounds having a low vapor pressure without additive of plasticisers. Furthermore, in DE-OS (German Published Specification) 3 611 137, only quite specific polyether block amides corresponding to the following formula

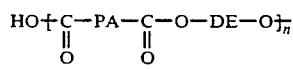

in which
PA denotes the polyamide part,
DE denotes the polyether part and
n represents an integer, which designates the number of the recurring unit, are ...

These polyether block amides have a specific block build-up, which results from the process for the preparation of polymers of this specific type. This specific process for the preparation of the specific polyether block amides is described in detail in claim 3 of DE-OS (German Published Specification) 3 611 137 and leads to polyether block amides having OH end groups.

It was surprising that polyether block amides having a different structure also allow non-volatile active compounds to migrate to the polymer surface from the polymer matrix without addition of plasticisers, since changing a single component of the overall system has unpredictable effects.

Polyether block amides which are suitable according to the invention are, for example, those which consist of polymer chains which are built up from recurring units corresponding to the formula I.

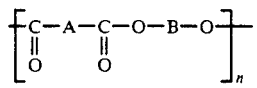 formula I

A is the polyamide chain derived from a polyamide having 2 carboxyl end groups by loss of the latter, B is the polyoxyalkylene glycol chain derived from a polyoxyalkylene glycol having terminal OH groups by loss of the latter and n is the number of units forming the polymer chain. Preferred end groups here are OH groups or radicals of compounds which interrupt the polymerization.

The dicarboxylic acid polyamides having the terminal carboxyl groups are obtained in a known manner, thus, for example, by polycondensation of one or more lactams and/or one or more amino acid, or furthermore by polycondensation of a dicarboxylic acid with a diamine, in each case in the presence of an excess of an organic dicarboxylic acid, preferably having terminal carboxyl groups.

These carboxylic acids become a constituent of the polyamide chain during the polycondensation and in particular add onto the end thereof, which gives an α-ω-dicarboxylic acid polyamide. The dicarboxylic acid furthermore acts as a chain-stopping agent, which is why it is also employed in excess.

The polyamide can be obtained starting from lactams and/or amino acids having a hydrocarbon chain consisting of 4–14 C atoms, such as, for example, from caprolactam, oenantholactam, dodecalactam, undecanolactam, decanolactam, 11-amino-undecano or 12-aminododecanoic acid.

Examples which may be mentioned without a limiting character for polyamides such as are formed by polycondensation of a dicarboxylic acid with a diamine are the condensation products of hexamethylenediamine with adipic, azelaic, sebacic and 1,12-dodecanedioic acid, and the condensation products of nonamethylenediamine and adipic acid.

Possible dicarboxylic acid used for synthesis of the polyamide, that is to say on the one hand for attaching in each case one carboxyl group to each end of the polyamide chain and on the other hand as chain-stopping agents, are those having 4–20 C atoms, in particular alkanedioic acids, such as succinic, adipic, suberic, azeleic, sebacic, undecanedioic or dodecanedioic acid, and furthermore cycloaliphatic or aromatic dicarboxylic acids, such as terephthalic or isphthalic, or cyclohexane-1,4-dicarboxylic acid.

The polyoxyalkylene glycols containing terminal OH groups are unbranched or branched and contain an alkylene radical having at least 2 C atoms. These are, in particular, polyoxyethylene glycol, polyoxypropylene glycol and polyoxytetramethylene glycol, and copolymers thereof.

The average molecular weight of these polyoxyalkylene glycols terminated by OH groups can vary within a wide range, and is advantageously between 100 and 6000, in particular between 200 and 3000.

The weight content of the polyoxyalkylene glycol, based on the total weight of the polyoxyalkylene glycol and dicarboxylic acid polyamide used for the preparation of the PEBA polymer, is 5–85 %, preferably 10–50 %.

Processes for the synthesis of such PEBA polymers are known from FR-PS 7 418 913 (Publication No. 2 273 021), DOS (German Published Specification) 2 802 989, DOS (German Published Specification) 2 837 687, DOS (German Published Specification) 2 523 991, EP-S 0 095 893, DOS (German Published Specification) 2 712 987 or DOS (German Published Specification) 2 716 004.

PEBA polymers which are preferably suitable according to the invention are those which, in contrast to those described above, are built up randomly. To prepare these polymers, a mixture of 1. one or more polyamide-forming compounds from the group comprising ω-aminocarboxylic acids and lactams having at least 10 carbon atoms, an α-ω-dihydroxy-polyoxyalkylene glycol, and 3. at least one organic dicarboxylic acid in a weight ratio of 1:(2+3) of between 30:70 and 98:2, hydroxyl and carbonyl groups being present in equivalent amounts (2+3), is heated to temperatures of between 23° C. and 30° C. in the presence of 2 to 30 percent by weight of water, based on the polyamide-forming compounds of group 1, under the autogenous pressure which is established, and, after removal of the water, the mixture is then further treated at 250° to 280° C. under normal pressure or under reduced pressure with exclusion of oxygen.

Such PEBA polymers which are preferably suitable are described, for example, in DE-OS (German Published Specification) 2,712,987.

PEBA polymers which are suitable and preferably suitable are obtainable, for example, under the commercial names PEBAX from Atochem, ®Vestamide from Hüls AG, ®Grilamid from EMS Chemie and ®Kellaflex from DSM.

Active compounds which may be mentioned for the shaped articles according to the invention are, preferably, insecticides, in particular parasiticides, for use on animals. The insecticides include phosphorus-containing compounds, such as phosphoric or phosphonic acid esters, naturally occurring and synthetic pyrethroids, carbamates, amidines, juvenile hormones and juvenoid synthetic active compounds.

The phosphoric or phosphoric acid esters include:

O-ethyl O-(8-quinolyl) phenyl-thiophosphate (quintiofos),

O-diethyl O-(3-chloro-4-methyl-7-coumarinyl) thiophosphate (coumaphos),

O.O-diethyl O-phenylglyoxylonitrile oxime thiophosphate (phoxim),

O,O-diethyl O-cyanochlorobenzaldoxime thiophosphate (chlorphoxim),

O.O-diethyl O-(4-bromo-2,5-dichlorophenyl) phosphorothionate (bromophos-ethyl),

O,O,O',O'-tetraethyl-S,S'-methylene di(phosphorodithionate) (ethion), 2,3-p-dioxanedithiol-S,S-bis(O,O-diethyl phosphorodithionate, 2-Chloro-1-(2,4-dichlorophenyl)-vinyl diethyl phosphate (chlorfenvinphos), and O,O-dimethyl O-(3-methyl-4-methylthiophenyl) thionophosphate (fenthion).

The carbamates include:

2-isopropoxyphenyl methylcarbamate (propoxur) and 1-naphthyl N-methylcarbamate (carbaryl).

The synthetic pyrethroids include compounds of the formula I formula I

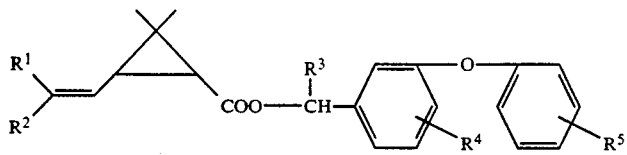

in which
- $R^1$ and $R^2$ represent halogen, optionally halogen-substituted alkyl or optionally halogen-substituted phenyl,
- $R^3$ represents hydrogen or CN,
- $R^4$ represents hydrogen or halogen and
- $R^5$ represents hydrogen or halogen, Preferred synthetic pyrethroids are those of the formula I in which
- $R^1$ represents halogen, in particular fluorine, chlorine or bromine,
- $R^2$ represents halogen, in particular fluorine, chlorine, bromine, trihalogenomethyl, phenyl or chlorophenyl,
- $R^3$ represents hydrogen or CN,
- $R^4$ represents hydrogen or fluorine and
- $R^5$ represents hydrogen.

Particularly preferred synthetic pyrethroids are those of the formula I in which
- $R^1$ represents chlorine,
- $R^2$ represents chlorine, trifluoromethyl or p-chlorophenyl,
- $R^3$ represents CN,
- $R^4$ represents hydrogen or fluorine and
- $R^5$ represents hydrogen.

Compounds of the formula I which may be mentioned in particular are those in which
- $R^1$ represents chlorine,
- $R^2$ represents chlorine or p-chlorophenyl,
- $R^3$ represents CN,
- $R^4$ represents fluorine in the 4-position and
- $R^5$ represents hydrogen.

Compounds which may be mentioned specifically are:

(α-cyano-4-fluoro-3-phenoxy)-benzyl 3-[2-(4-chlorophenyl]-2-chlorovinyl]-2,2-dimethyl-cyclopropanecarboxylate (flumethrin), α-cyano(4-fluoro-3-phenoxy)-benzyl 2,2-dimethyl-3-(2,2-dichlorovinyl)-cyclopropanecarboxylate (cyfluthrin) and its enantiomers and stereomers, α-cyano-3-phenoxybenzyl (±)-cis,trans-3-(2,2-dibromovinyl)-2,2 -dimethylcyclopropanecarboxylate (deltamethrin), α-cyano-3-phenoxybenzyl 2,2-dimethyl-3-(2,2-dichlorovinyl)-cyclopropanecarboxylate (cypermethrin), 3-phenoxybenzyl (±)-cis,trans-3-(2,2-dichlorovinyl)-2,2-dimethylcyclopropanecarboxylate (permethrin), α-cyano-3-phenoxy-benzyl α-(p-Cl-phenyl)-isovalerate (fenvalerate) and 2-cyano-3-phenoxybenzyl 2-(2-chloro-α,α,α-trifluoro-p-toluidino)-3-methylbutyrate (fluvalinate).

The amidines include:

3-methyl-2-[2,4-dimethyl-phenylimino]-thiazoline, 2-(4-chloro-2-methylphenylimino)-3-methylthiazolidine, 2-(4-chloro-2-methylphenylimino)-3-(isobutyl-1-enyl)-thiazolidine and 1,5-bis-(2,4-dimethylphenyl)-3-methyl-1,3,5-triazapenta-1,4-diene (amitraz).

The juvenile hormones or substances like juvenile hormones include substituted diaryl ethers, benzoylureas and triazine derivatives. The juvenile hormones and substances like juvenile hormones include, in particular, compounds of the following formulae:

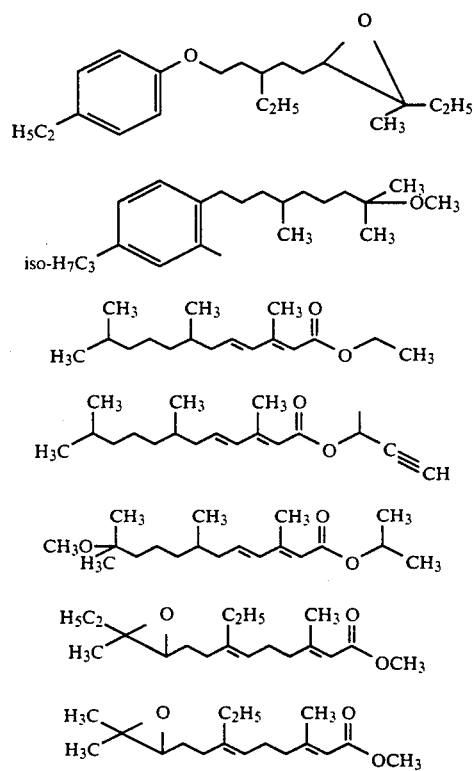

The substituted diaryl ethers include, in particular, substituted alkoxydiphenyl ethers or -diphenylmethanes of the general formula I

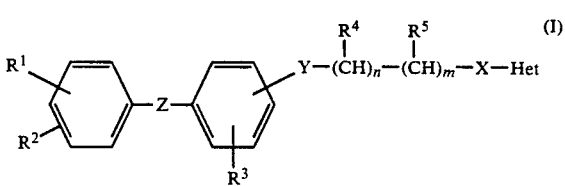

wherein
- $R^1$ represents hydrogen, halogen, alkyl, alkoxy, alkylthio, halogenoalkyl, halogenoalkoxy, halogenoalkylthio, dioxyalkylene, dioxyhalogenoalkylene, CN, $NO_2$, alkenyl, alkinyl, alkoxyalkyl, alkoxyalkoxy or hydroxyalkoxy, $R^2$ represents the radicals mentioned for $R^1$,
$R^3$ represents the radicals mentioned for $R^1$,
$R^4$ represents hydrogen, alkyl, halogenoalkyl or halogen,
$R^5$ represents the radicals mentioned for $R^4$,
Het represents optionally substituted heteroaryl, which is not bonded to the rest of the radical via the hetero atom,
X and Y independently of one another represent —O— or —S—,
Z represents —O—, —S—, —CH$_2$—, —CHCH$_3$— or —C(CH$_2$)$_2$— and
m and n independently of one another represent 0, 1, 2 or 3, but their sum is equal to or greater than 2.

Particularly preferred compounds of the formula I are those
in which
$R^1$ represents hydrogen, methyl, trifluoromethyl, methoxy, trifluoromethoxy, chlorine or fluorine
$R^2$ represents hydrogen,
$R^3$ represents hydrogen, fluorine, chlorine or methyl,
$R^4$ represents hydrogen or methyl,
$R^5$ represents methyl, ethyl, trifluoromethyl or hydrogen,
Het represents pyridyl or pyridazinyl, which are optionally substituted by fluorine, chlorine, methyl, NO$_2$, methoxy or methylmercapto,
X represents O,
Y represents O,
Z represents O, CH$_2$ or —C(CH$_3$)$_2$—,
m represents 1 and
n represents 1.

The following compounds may be mentioned specifically:

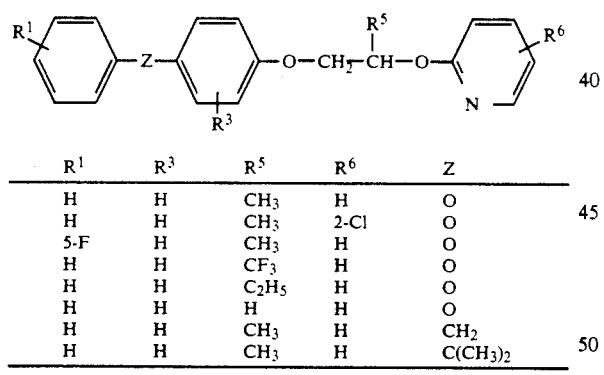

| $R^1$ | $R^3$ | $R^5$ | $R^6$ | Z |
|---|---|---|---|---|
| H | H | CH$_3$ | H | O |
| H | H | CH$_3$ | 2-Cl | O |
| 5-F | H | CH$_3$ | H | O |
| H | H | CF$_3$ | H | O |
| H | H | C$_2$H$_5$ | H | O |
| H | H | H | H | O |
| H | H | CH$_3$ | H | CH$_2$ |
| H | H | CH$_3$ | H | C(CH$_3$)$_2$ |

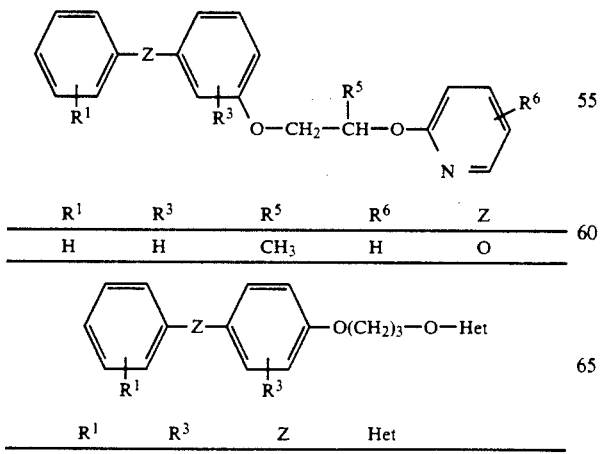

| $R^1$ | $R^3$ | $R^5$ | $R^6$ | Z |
|---|---|---|---|---|
| H | H | CH$_3$ | H | O |

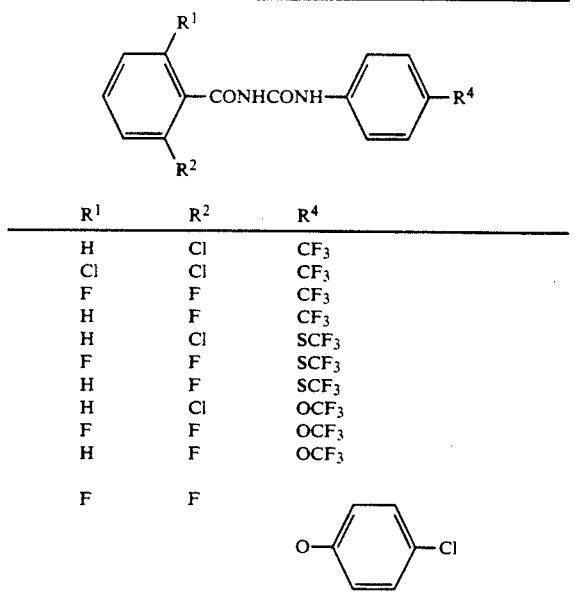

| $R^1$ | $R^3$ | Z | Het |
|---|---|---|---|
| H | H | O | 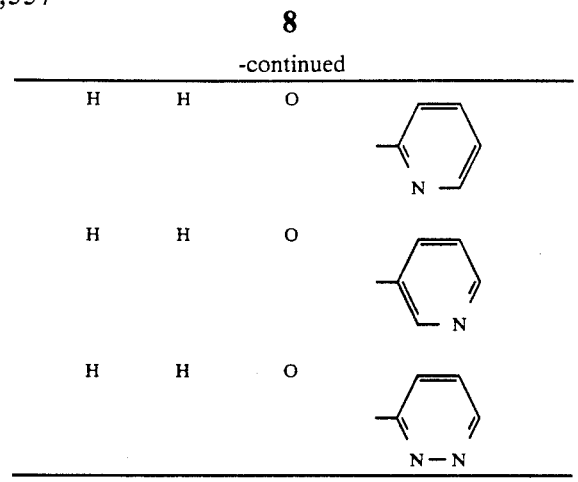 |
| H | H | O | |
| H | H | O | |

The benzoylureas include compounds of the formula (V):

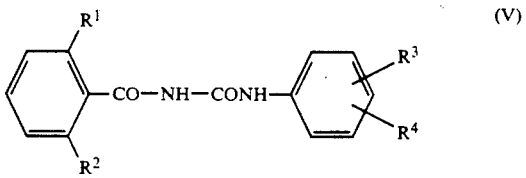

wherein
$R^1$ represents halogen,
$R^2$ represents hydrogen or halogen,
$R^3$ represents hydrogen, halogen or C$_{1-4}$-alkyl and
R$_4$ represents halogen, 1-5-halogeno-C$_{1-4}$-alkyl, C$_{1-4}$-alkoxy, 1-5-halogeno-C$_{1-4}$-alkoxy, C$_{1-4}$-alkylthio, 1-5-halogeno-C$_{1-4}$-alkylthio, phenoxy or pyridyloxy, which can optionally be substituted by halogen, C$_{1-4}$-alkyl, 1-5-halogeno-C$_{1-4}$-alkyl, C$_{1-4}$-alkoxy, 1-5-halogeno-C$_{1-4}$-alkoxy, C$_{1-4}$-alkylthio or 1-5-halogeno-C$_1$-C$_4$-alkylthio.

The following compounds may be mentioned in particular:

| $R^1$ | $R^2$ | $R^4$ |
|---|---|---|
| H | Cl | CF$_3$ |
| Cl | Cl | CF$_3$ |
| F | F | CF$_3$ |
| H | F | CF$_3$ |
| H | Cl | SCF$_3$ |
| F | F | SCF$_3$ |
| H | F | SCF$_3$ |
| H | Cl | OCF$_3$ |
| F | F | OCF$_3$ |
| H | F | OCF$_3$ |
| F | F | (O—⌬—Cl) |

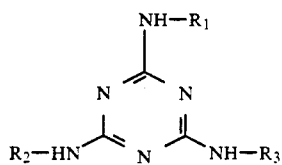

| R¹ | R² | R⁴ |
|---|---|---|
| F | F | -O-⟨⟩-CF₃ (para) |
| F | F | -O-⟨⟩-CF₃ (para) |

The triazines include compounds of the formula (VI)

$$\underset{R_2-HN}{\overset{NH-R_1}{\underset{N}{\overset{N}{\bigtriangleup}}}}\overset{}{NH-R_3} \quad (VI)$$

wherein $R_1$ represents cyclopropyl or isopropyl;

$R_2$ denotes hydrogen, halogen, $C_1-C_{12}$-alkylcarbonyl, cyclopropylcarbonyl, $C_1-C_{12}$-alklcarbamoyl, $C_1-C_{12}$-alkylthiocarbamoyl or $C_2-C_6$-alkenylcarbamoyl; and $R_3$ represents hydrogen, $C_1-C_{12}$-alkyl, cyclopropyl, $C_2-C_6$-alkenyl, $C_1-C_{12}$-alkylcarbonyl, cyclopropylcarbonyl, $C_1-C_{12}$-alkylcarbamoyl, $C_1-C_{12}$-alkylthiocarbamoyl or $C_2-C_6$-alkenylcarbamoyl, and acid addition salts thereof which are non-toxic to warm-blooded animals.

Compounds which may be mentioned in particular are:

| $R_1$ | $R_2$ | $R_3$ |
|---|---|---|
| Cyclopropyl | H | H |
| Cyclopropyl | H | CH₃ |
| Cyclopropyl | H | C₂H₅ |
| Cyclopropyl | H | C₃H₇-n |
| Cyclopropyl | H | C₄H₉-n |
| Cyclopropyl | H | C₅H₁₁-n |
| Cyclopropyl | H | C₆H₁₃-n |
| Cyclopropyl | H | C₇H₁₅-n |
| Cyclopropyl | H | C₈H₁₇-n |
| Cyclopropyl | H | C₁₂H₂₅-n |
| Cyclopropyl | H | CH₂-C₄H₉-t |
| Cyclopropyl | H | CH₂CH(CH₃)C₂H₅ |
| Cyclopropyl | H | CH₂CH=CH₂ |
| Cyclopropyl | Cl | C₂H₅ |
| Cyclopropyl | Cl | C₆H₁₃-n |
| Cyclopropyl | Cl | C₈H₁₇-n |
| Cyclopropyl | Cl | C₁₂H₂₅-n |
| Cyclopropyl | H | Cyclopropyl |
| Cyclopropyl | H | COCH₃ |
| Cyclopropyl | H | COCH₃.HCl |
| Cyclopropyl | H | COC₂H₅.HCl |
| Cyclopropyl | H | COC₂H₅ |
| Cyclopropyl | H | COC₃H₇-n |
| Cyclopropyl | H | COC₃H₇-i |
| Cyclopropyl | H | COC₄H₉-t.HCl |
| Cyclopropyl | H | COC₄H₉-n |
| Cyclopropyl | H | COC₆H₁₃-n |
| Cyclopropyl | H | COC₁₁-H₂₃-n |
| Cyclopropyl | COCH₃ | COC₂H₅ |
| Cyclopropyl | COC₃H₇-n | COC₆H₁₃-n |
| Cyclopropyl | COCH₃ | COC₃H₇-n |
| Cyclopropyl | COC₂H₅ | COC₃H₇-n |
| Cyclopropyl | H | COCyclopropyl |
| Cyclopropyl | COCylcopropyl | COCyclopropyl |
| Cyclopcopyl | COCH₃ | COCH₃ |
| Isopropyl | H | H |
| Isopropyl | H | COCH₃ |
| Isopropyl | H | COC₃H₇-n |
| Cyclopropyl | H | CONHCH₃ |
| Cyclopropyl | H | CONHC₃H₇-i |
| Cyclopropyl | CONHCH₃ | CONHCH₃ |
| Cyclopropyl | H | CSNHCH₃ |
| Cyclopropyl | H | CONHCH₂CH=CH₂ |
| Cyclopropyl | CONHCH₂CH=CH₂ | CONHCH₂CH=CH₂ |
| Cyclopropyl | CSNHCH₃ | CSNHCH₃ |

The active compounds having the common names propoxur, cyfluthrin, flumethrin, pyriproxyfen, methoprene, Diazinon, amitraz and fenthion may be singled out in particular.

The active compounds can be present in the shaped articles by themselves or as a mixture with one another.

The active compounds are present in the shaped articles in concentrations of 0.1–20 % by weight, preferably of between 1 and 10 % by weight.

The shaped articles according to the invention can furthermore comprise the additives customary for plastics. Customary additives are, for example, pigments, stabilizers, flow agents, lubricants and mold release agents.

Examples of customary additives are:

1. Antioxidants 1.1 Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-di-cyclopentyl-4-methylphenol, 2-(α-methyl-cyclohexyl)-4,6-dimethylphenol, 2,6-di-octadecyl-4-methylphenol and 2,4,6-tricyclohexylphenol, 2,6-di-tert-butyl-4-methoxymethylphenol.

1.2 Alkylated hydroquinones, for example 2,6-di-tert-butyl-4-methoxyphenol, 2,5-di-tert-butyl-hydroquinone, 2,5-di-tert-amyl-hydroquinone and 2,6-diphenyl-4-octadecyloxyphenyl.

1.3 Hydroxylated thiodiphenyl ethers, for example 2,2'-thio-bis-(6-tert-butyl-4-methylphenol), 2,2,-thiobis-(4-octylphenol), 4,4,-thio-bis-(6-tert-butyl-3methylphenol) and 4,4'-thio-bis-(6-tert-butyl-2-methylphenol).

1.4 Alkylidene-bisphenols, for example 2,2,-methylene-bis-(6-tert-butyl-4-methylphenol), 2,2'-methylenebis-(6-tert-butyl-4-ethylphenol), 2,2'-methylene-bis-(4-methyl-6(α-methylcyclohexyl)phenol, 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert-butylphenol), 4,4'-methylene-bis-(6-tert-butyl-2-methylphenol), 1,1-bis-(5-tert-butyl-4- hydroxy-2-methylphenyl)-butane, 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)butyrate], di-(3-tert-butyl-4-hydroxy-5-methylphenyl)-dicyclopentadiene and di-[2-(3'-tert-butyl-2'-hydroxy-5'-methylbenzyl)-6-tert-butyl-4-methylphenyl] terephthalate.

1.5 Benzyl compounds, for example 1,3,5-tri-(3,5-di-tert-butyl-4-hydroxybenzyl)-2,4,6-trimethylbenzene, di-(3,5-di-tert-butyl-4-hydroxybenzyl) sulphide, isooctyl 3,5-di-tert-butyl-4-hydroxybenzyl-mercaptoacetate, bis-(4-tert-butyl-3-hydroxy-2,6-dimethylbenzyl) dithiol-terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzylphosphonate and 3,5-di-tert-butyl-4-hydroxybenzylphosphonic acid monoethyl ester calcium salt.

1.6 Acylaminophenols, for example 4-hydroxy-lauric acid anilide, 4-hydroxystearic acid anilide, 2,4-bis-octylmercapto-6-(3,5-di-tert-butyl-4-hydroxyanilino)-s-triazine and octyl N-(3,5-di-tert-butyl-4-hydroxyphenyl)-carbamate.

1.7 Esters of $\beta$-(3,5-di-tert-butyl-4-hydroxyphenyl)propionic acid with mono- or polyhydric alcohols, such as, for example, methanol, octadecanol, 1,6-hexanediol, neopentyl glycol, thiodiethylene glycol, diethylene glycol, triethylene glycol, pentaerythritol, tris-hydroxyethyl isocyanurate and di-hydroxyethyl-oxalic acid diamide.

1.8 Esters of $\beta$-(5-tert-butyl-4-hydroxy-3-methylphenyl)propionic acid with mono- or polyhydric alcohols, such as, for example, with methanol, octadecanol, 1,6-hexanediol, neopentyl glycol, thiodiethylene glycol, diethylene glycol, triethylene glycol, pentaerythritol, tris-hydroxyethyl isocyanurate and di-hydroxyethyl-oxyalic acid diamide.

1.9 Amides of $\beta$-(3,5-di-tert-butyl-4-hydroxyphenyl)-propionic acid, such as, for example, N,N'-di-(3,5-di-tert-butyl-4-hydroxyphenylpropionyl)-hexamethylenediamine, N,N'-(3,5-di-tert-butyl-4-hydroxyphenylpropionyl)-trimethylenediamine and N,N'-di-(3,5-di-tert-butyl-4-hydroxyphenylpropionyl)-hydrazine.

2. UV absorbers and light stabilizers 2.1 2-(2'-Hydroxyphenyl)-benzotriazoles, such as, for example, the 5'-methyl, 3',5'-di-tert-butyl, 5'-tert-butyl, 1,5'-(1,1,3,3-tetramethylbutyl),5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis-($\alpha,\alpha$-dimethylbenzyl) derivative.

2.2 2-Hydroxybenzophenones, such as, for example, the 4-hydroxy, 4-methoxy, 4-octoxy, 4-decyloxy, 4-dodecyloxy, 4-benzyloxy, 4,2',4'-trihydoxy and 2'-hydroxy-4,4,-dimethoxy derivative.

2.3 Esters of optionally substituted benzoic acids, such as, for example, 4-tert-butyl-phenyl salicylate, phenyl salicylate, octylphenyl salicylate, dibenzoylresorcinol, bis-(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4 Acrylates, such as, for example, ethyl or isooctyl $\alpha$-cyano-$\beta,\beta$-diphenylacrylate,methyl $\alpha$-carbomethoxycinnamate, methyl or butyl $\alpha$-cyano-$\beta$-methyl-p-methoxy-cinnamate, methyl $\alpha$-carbomethoxy-p-methoxycinnamate and N-($\beta$-carbomethoxy-$\beta$-cyanovinyl)-2-methyl-indoline.

2.5 Nickel compounds, such as, for example, nickel complexes of 2,2'-thio-bis-[4-(1,1,3,3-tetramethylbutyl)-phenol], such as the 1:1 or 1:2 complex, optionally with additional ligands, such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl or ethyl ester, nickel complexes of ketoximes, such as 2-hydroxy-4-methyl-phenyl undecyl ketone oxime, and nickel complexes of 1-phenyl-4-lauroyl-5-hydroxypyrazole, optionally with additional ligands.

2.6 Sterically hindered amines, such as, for example, bis-(2,2,6,6-tetramethylpiperidyl) sebacate, bis-(1,2,2,6,6-pentamethylpiperidyl) sebacate, bis-(1,2,2,6,6-pentamethylpiperidyl) n-butyl-3,5-di-tert-butyl-4-hydroxybenzyl-malonate, the condensation product of 1-hydroxyethyl-2,2,6,6-tetramethyl-4-hydroxypiperidine and succinic acid, the condensation product of N,N'-(2,2,6,6-tetramethyl-4-piperidyl)-hexamethylenediamine and 4-tert-octylamino-2,6-dichloro-1,3,5-s-triazine. tris-(2,2,6,6-tetramethyl-4-piperidyl) nitrotriacetate, tetrakis-(2,2,6,6-tetramethyl-4-piperidyl)-1,2,3,4-butanetetracarboxylic acid and 1,1,-(1,2-ethanediyl)-bis-(3,3,5,5-tetramethylpiperazinone).

2.7 Oxalic acid diamides, such as, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethyl-aminopropyl)-oxalamide, 2-ethoxy-5-tert-butyl-2'-ethyloxanilide and its mixture with 2-ethoxy-2'-ethyl-5,4'-di-tert-butyl-oxanilide and mixtures of o- and p-methoxy- and of o- and p-ethoxy-disubstituted oxanilides.

3. Metal deactivators, such as, for example, N,N'-diphenyloxalic acid diamide, N-salicylal-N'-salicyloylhydrazine, N,N'-bis-(salicyloylhydrazine, N,N'-bis-(3,5-di-tert-butyl-4-hydroxyphenylpropionyl)-hydrazine, 3-salicyloylamino-1,2,4-triazole and bis-benzylidene-oxalic acid dihydrazide.

4. Phosphites and phosphonites, such as, for example, triphenyl phosphite, diphenyl alkyl phosphites, phenyl dialkyl phosphites, tri-(nonylphenyl) phosphite, trilauryl phosphite, trioctadecyl phosphite, distearyl pentaerythritol diphosphite, tris-[2,4-di-tert-butylphenyl)-phosphite, diisodecylpentaerythritol diphosphite, di-(2,4-di-tert-butylphenyl)-pentaerythritol diphosphite, tristearyl-sorbitol triphosphite, tetrakis-[2,4-di-tert-butylphenyl]- 4,4'-biphenylene diphosphonite and 3,9-bis-(2,4-di-tert-butylphenoxy-2,4,8,10-tetraoxa-3,9-diphosphaspiro[5,5]undecane.

5. Peroxide-destroying compounds, such as, for example, esters of $\beta$-thiodipropionic acid, for example the lauryl, stearyl, myristyl or tridecyl ester, mercaptobenzimidazole, the zinc salt of 2-mercaptobenzimidazole, zinc dibutyl-dithiocarbamate, dioctadecyl disulphide and pentaerythritol tetrakis($\beta$-dodecylmercapto)-propionate.

6. Polyamide stabilizers, such as, for example, copper salts in combination with iodides and/or phosphorus compounds, and salts of divalent manganese.

7. Basic costabilizers, such as, for example, melamine, polyvinylpyrrolidone, dicyandiamide, triallyl cyanurate, urea derivatives, amines, polyamides, polyurethanes and alkali metal and alkaline earth metal salts of higher fatty acids, for example Ca stearate, Zn stearate, Mg stearate, Na riconoleate, K palmitate, antimony pyrocatecholate or tin pyrocatecholate.

8. Nucleating agents, such as, for example, 4-tert-butylbenzoic acid, adipic acid and diphenylacetic acid.
9. Fillers and reinforcing agents, such as, for example, calcium carbonate, silicates, glass fibers, asbestos, talc, kaolin, mica, barium sulphate, metal oxides and hydroxides, carbon black and graphite.
10. Other additives, such as, for example, plasticisers, lubricants, emulsifiers, pigments, optical brighteners, flameproofing agents, antistatics and blowing agents.

The shaped articles according to the invention are obtained by mixing the individual components. Mixing can be carried out by known techniques in any manner, for example via kneaders or extruders. Further processing is carried out by the known techniques of thermoplastic processing, for example by extrusion or injection molding.

Shaped articles according to the present invention are neck collars, neck collar pendants (medallions}, ear, tail and foot tapes, ear marks, films, peel-off films, adhesive strips, strips, sheets and granules. Neck collars and medallions for dogs and cats may be mentioned as preferred.

The shaped articles are used for combating parasites on environment of the host animals, such as domestic animals, pets and stock animals.

The domestic animals, pets and stock animals include mammals, such as, for example, cattle, sheep, goats, horses, pigs, dogs and cats.

The pests include:

From the order of the Anoplura, for example, Haematopinus spp., Linognathus spp., Solenopotes spp., Pediculus spp. and Pthirus spp.;

from the order of the Mallophaga, for example, Trimenopon spp., Menopon spp., Eomenacanthus spp., Menacanthus spp., Trichodectes spp., Felicola spp., Damalinea spp. and Bovicola spp.;

from the order of the Diptera, for example, Aedes spp., Culex spp., Simulium spp., Phlebotomus spp., Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Hypoderma spp., Oestrus spp., Rhinoestrus spp., Melophagus spp. and Hippobosca spp..

From the order of the Siphonaptera, for example, Ctenocephalides spp., Echidnophaga spp., Ceratophyllus spp..

From the order of the Metastigmata, for example, Hyalomma spp., Rhipicephalus spp., Boophilus spp., Amblyomma spp., Haemaphysalis spp., Dermacentor spp., Ixodes spp., Argas spp., Ornithodorus spp. and Otobius spp.;

from the order of the Mesostigmata, for example, Dermanyssus spp., Ornithonyssus spp. and Pneumonyssus spp..

From the order of the Prostigmata, for example, Cheyletiella spp., Psorergates spp., Myobia spp., Demodex spp. and Neotrombicula spp.;

from the order of the Astigmata, for example, Acarus spp., Myocoptes spp., Psoroptes spp., Chorioptes spp., Otodectes spp., Sarcoptes spp., Notoedres spp., Knemidocoptes spp., Neoknemidocoptes spp. Cytodites spp. and Laminosioptes spp..

The following examples of insecticidal moldings based on copolyether block amides are intended to illustrate the invention without limiting it:

| Example A | | |
|---|---|---|
| Composition: | β-Cyfluthrin | 10.00 g |
| | Pyriproxifen | 0.35 g |
| | Triacetin | 5.00 g |
| | Polyether block amide (Pebax ®) | 84.65 g |
| | | 100.00 g |

Production:

The active compounds and triacetin are heated together until a clear solution results. Pebax is wetted with the warm solution of active compounds and triacetin in a mixer. The components are mixed until the mixture is homogeneous. Heating the mixture, for example as a result of increasing the speed of rotation of the mixer, promotes absorption of the solution into the polyether block sheets, from which medallions (=pendants for neck collars) of 2×4 cm are stamped.

| Example B | | |
|---|---|---|
| Composition: | Propoxur | 7.50 g |
| | Polyether block amide (Pebax ®) | 92.50 g |
| | | 100.00 g |

Production:

The active compound is applied to the carrier in an intensive mixer and the mixture is shaped to form neck collars for dogs by injection greeting.

| Example C | | |
|---|---|---|
| Composition: | β-Cyfluthrin | 12.00 g |
| | Polyether block amide (Vestamide ®) | 88.00 g |
| | | 100.00 g |

Production:

The mixture is extruded to form neck collars for dogs in a conventional manner.

We claim:

1. Shaped articles which contain active compounds, characterized in that they consist essentially of, as the carrier, thermoplastic elastomers based on polyether block amides and, as the active compounds, insecticides or acaricides having vapor pressures below about $1.3\times10^{-5}$ mbar at 20° C., an optionally containing additives, said shaped articles having significantly improved flea-killing capacity as compared to shaped articles having the same carrier but active compounds with vapor pressures above about $1.3\times10^{-5}$ mbar at 20° C. instead of said active compounds having vapor pressures below about $1.3\times10^{-5}$ mbar at 20° C.

2. Articles according to claim 1 in the form of animal collars, medaillons, ear-marks.

3. Shaped articles according to claim 1 in which polyether block amides consist of polymer chains which are built up from recurring units corresponding to the formula I:

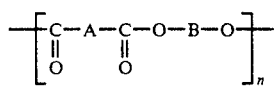

formula I in which
A is the polyamide chain derived from a polyamide having 2 carboxyl end groups by loss of the latter,
B is the polyoxyalkylene glycol chain derived from a polyoxyalkylene glycol having terminal OH groups by loss of the latter and
n is the number of units forming the polymer chain. Preferred end groups here are OH groups or radicals of compounds which interrupt the polymerization.

4. Shaped articles according to claim 1 in which the polyether block amide is produced by polycondensation of polyamides from lactams and/or amino acids having a hydrocarbon chain consisting of 4–14 C-atoms, such as, for example, from caprolactam, oenantholactam, dodecalactam, undecanolactam, decanolactam, 11-amino-undecano or 12-aminododecanoic acid or from polycondensation of diamines and dicarboxylic acids, in particular alkanedioic acids, such as succinic, adipic, suberic, azeleic, sebacic, undecanedioic or dodecanedioic acid, such as terephthalic or isphthalic, or cyclohexane-1,4-dicarboxylic acid.

5. Shaped articles according to claim 1 in which the polyether block amides of the invention are those which are built up randomly when a mixture of
  1. one or more polyamide-forming compounds from the group comprising ω-aminocarboxylic acids and lactams having at least 10 carbon atoms,
  2. an α-ω-dihydroxy-polyoxyalkylene glycol, and
  3. at least one organic dicarboxylic acid
  in a weight ratio of 1:(2+3) of between 30:70 and 98:2, hydroxyl and carbonyl groups being present in equivalent amounts (2+3), is heated to temperatures of between 23° C. and 30° C. in the presence of 2 to 30 percent by weight of water, based on the polyamide-forming compounds of group 1, under the autogenous pressure which is established, and, after removal of the water, the mixture is then further treated at 250° to 280° C. under normal pressure or under reduced pressure with exclusion of oxygen.

6. Shaped articles according to claim 1 in which the active compounds are insecticides, selected from phosphoric or phosphonic acid esters, synthetic pyrethroids, carbamates, amidines, juvenile hormones and synthetic juvenoid active compounds.

7. Shaped articles according to claim 1 in which the active compounds are carbamates such as 2-isopropoxyphenyl methylcarbamate (propoxur) and
1-naphthyl N-methylcarbamate (carbaryl) and synthetic pyrethroids of the formula I

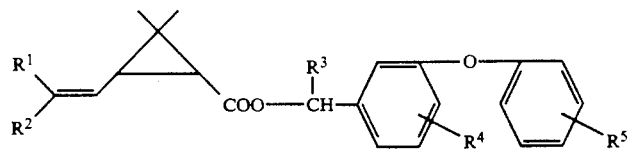

formula I in which
R¹ and R² represent halogen, optionally halogen-substituted alkyl or optionally halogen-substituted phenyl,
R³ represents hydrogen or CN,
R⁴ represents hydrogen or halogen and
R⁵ represents hydrogen or halogen, 8. Shaped articles according to claim 1 in which the active compounds are substituted alkoxydiphenyl ethers or -diphenylmethanes of the general formula I

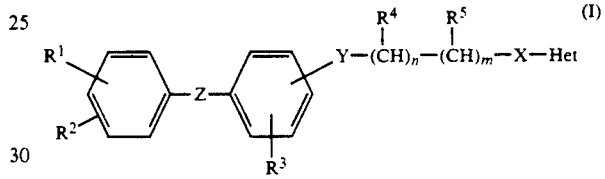

wherein
R¹ represents hydrogen, halogen, alkyl, alkoxy, alkylthio, halogenoalkyl, halogenoalkoxy, halogenoalkylthio, dioxyalkylene, dioxyhalogenoalkylene, CN, NO₂, alkenyl, alkinyl, alkoxyalkyl, alkoxyalkoxy or hydroxyalkoxy,
R² represents the radicals mentioned for R¹,
R³ represents the radicals mentioned for R¹,
R⁴ represents hydrogen, alkyl, halogenoalkyl or halogen,
R⁵ represents the radicals mentioned for R⁴,
Het represents optionally substituted heteroaryl, which is not bonded to the rest of the radical via the heteroatom.

9. Shaped articles according to claim 1 in which the active compounds are propoxur, cyfluthrin, flumethrin, pyriproxyfen, methoprene, diazinon, amitraz.

10. Shaped articles according to claim 1 which contain active compounds characterized in that they consist essentially of, as the carrier, thermoplastic elastomers based on polyether block amides and, as the active compound a member selected from the group consisting of propoxur, cyfluthrin, flumethrin and mixtures thereof, an optionally containing additives.

11. Shaped articles in accordance with claim 11, wherein said active compound is propoxur.

12. Shaped articles in accordance with claim 11, wherein said active compound is Cyfluthrin.

13. Shaped articles in accordance with claim 11, wherein said active compound is Flumethrin.

* * * * *

UNITED STATES PATENT AND TRADEMARK OFFICE
CERTIFICATE OF CORRECTION

PATENT NO : 5,310,557
DATED : May 10, 1994
INVENTOR(S): Heinz-Dieter Brandt, et al.

It is certified that error appears in the above-identified patent and that said Letters Patent are hereby corrected as shown below:

Col. 16, Claim 11, Line 1     After "Claim" Delete "11" and
Col. 16, Claim 12, Line 1      Substitute --10--
Col. 16, Claim 13, Line 1

Signed and Sealed this

Twenty-first Day of September, 1999

Attest:

Q. TODD DICKINSON

*Attesting Officer*     *Acting Commissioner of Patents and Trademarks*